(12) United States Patent
Poor et al.

(10) Patent No.: US 6,607,496 B1
(45) Date of Patent: Aug. 19, 2003

(54) STEERABLE STYLET WITH ENHANCED TORSIONAL TRANSFER STRENGTH

(75) Inventors: Corinne A. G. Poor, Roseville, MN (US); Kenneth C. Gardeski, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 145 days.

(21) Appl. No.: 09/659,286

(22) Filed: Sep. 12, 2000

(51) Int. Cl.$^7$ ................................................. A61B 5/00
(52) U.S. Cl. ........................................................ 600/585
(58) Field of Search ................................. 600/433, 434, 600/435; 604/523–532; 607/122, 123, 125, 126

(56) References Cited

U.S. PATENT DOCUMENTS

| | | |
|---|---|---|
| 4,381,013 A | 4/1983 | Dutcher |
| 4,452,254 A | 6/1984 | Goldberg et al. |
| 4,677,990 A | 7/1987 | Neubauer |
| 4,846,175 A | 7/1989 | Frimberger |
| 5,396,902 A | 3/1995 | Brennen et al. |
| 5,674,271 A | 10/1997 | Denker |
| 5,690,611 A | 11/1997 | Swartz et al. |
| 6,027,462 A | 2/2000 | Greene et al. |
| 6,096,036 A | 8/2000 | Bowe et al. |

FOREIGN PATENT DOCUMENTS

| WO | WO 01/89626 | 11/2001 |
|---|---|---|

*Primary Examiner*—Eric F. Winakur
*Assistant Examiner*—Pamela L Wingood
(74) *Attorney, Agent, or Firm*—Girma Wolde-Michael; Michael G. Soldner

(57) ABSTRACT

A steerable guidewire or stylet that has increased torsional strength is disclosed. A braided structure located in the vicinity of at least the distal end of the guidewire or stylet provides for a more efficient transfer of rotational force over the length of the guidewire or stylet. The braided structure may be comprised of a flat metal ribbon wire that may optionally be reinforced with a polyimide. According to one aspect of the invention, the stylet includes an outer member, and a pull-wire located within the outer member. The pull-wire is coupled to the distal tip of the outer member such that when tension is applied to the pull-wire, the distal tip of the outer member is deflected. The distal tip of the outer member may be formed of a material having superelastic properties such as a nickel titanium alloy, whereas the proximal portion of the stylet may be formed of a material having more torsional strength. The distal tip of the outer member may further include at least one aperture to provide a preferred bending direction when tension is applied to the pull-wire. Pull-wire is retained within the at least one aperture by the braided structure. According to another aspect of the invention, a handle is provided that includes both rotatable and slidable mechanisms to facilitate deflection of the distal tip portion of the outer member. In one embodiment, the handle may be adapted for use with a lead extension tool.

23 Claims, 14 Drawing Sheets

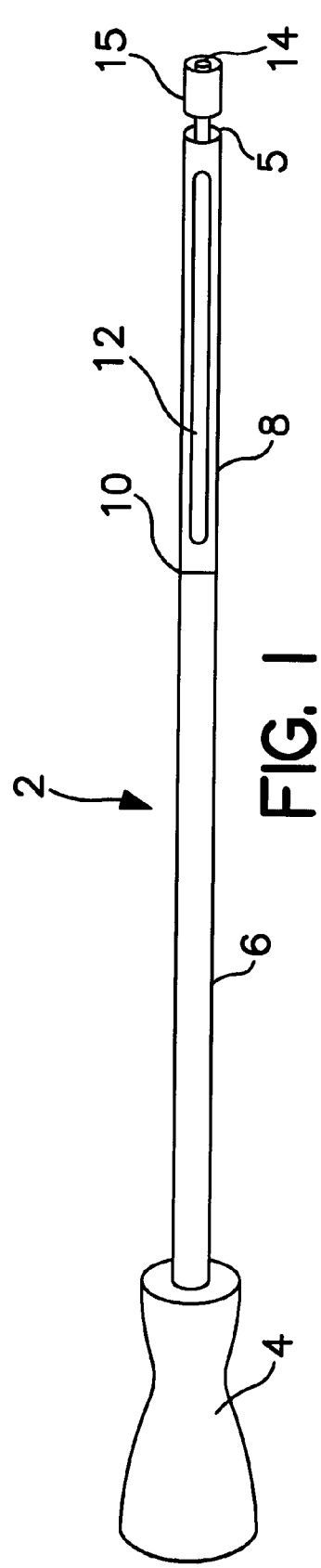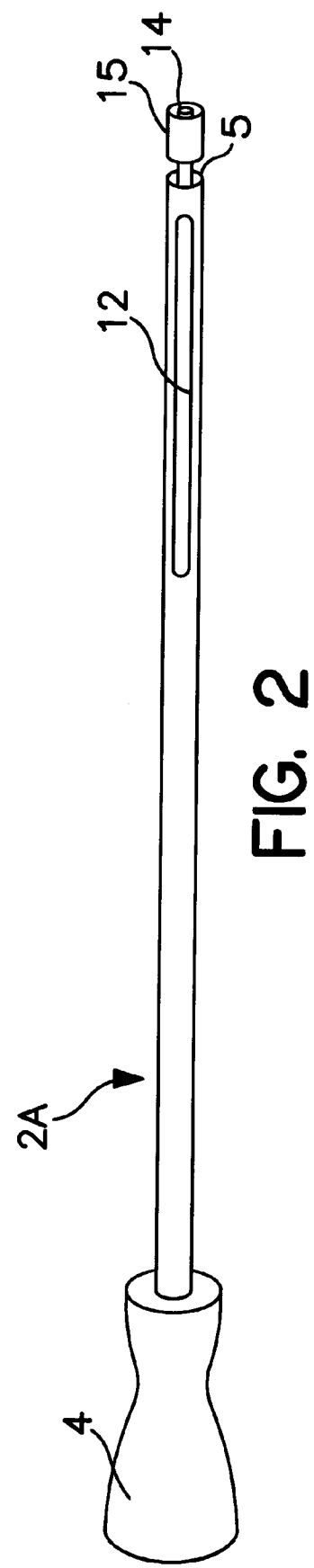

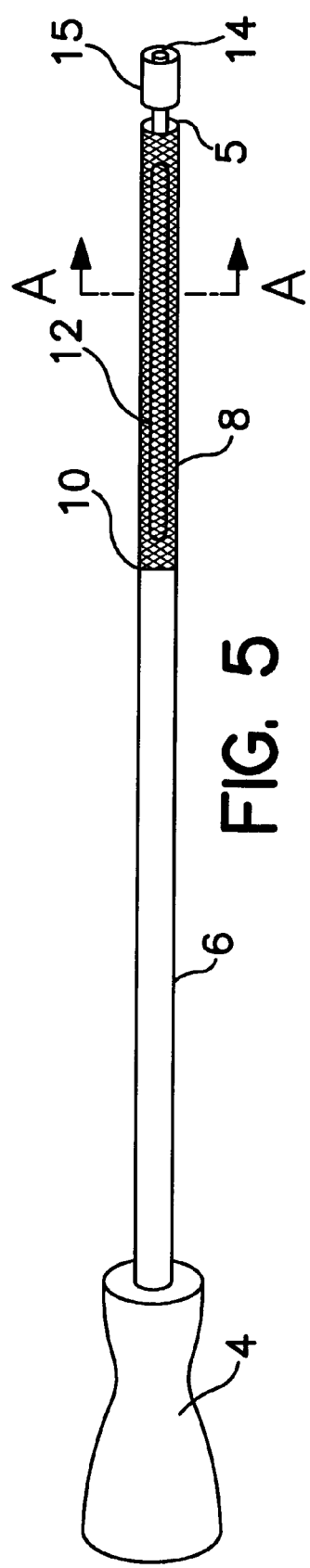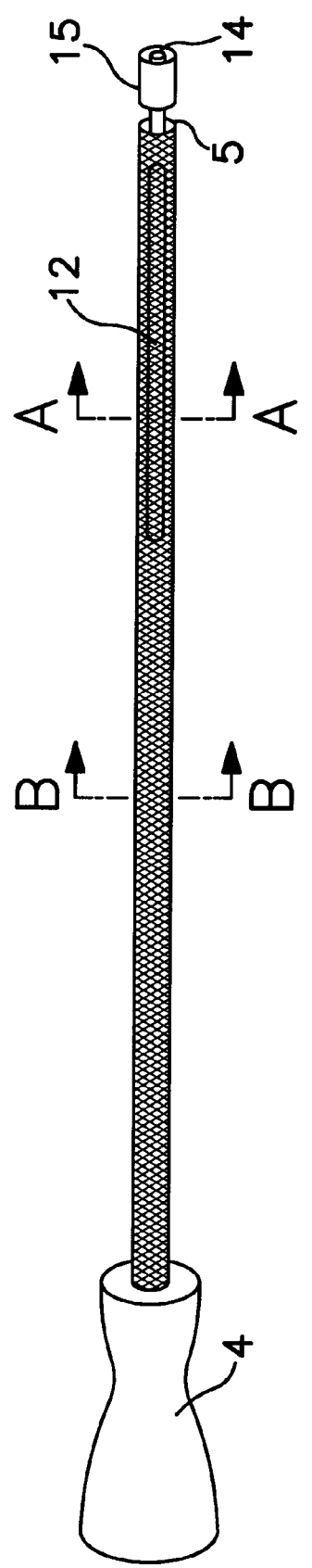

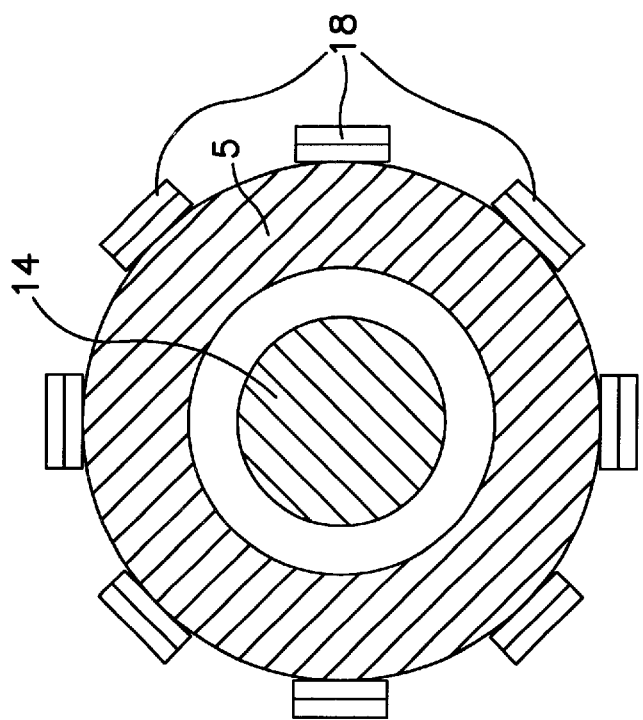
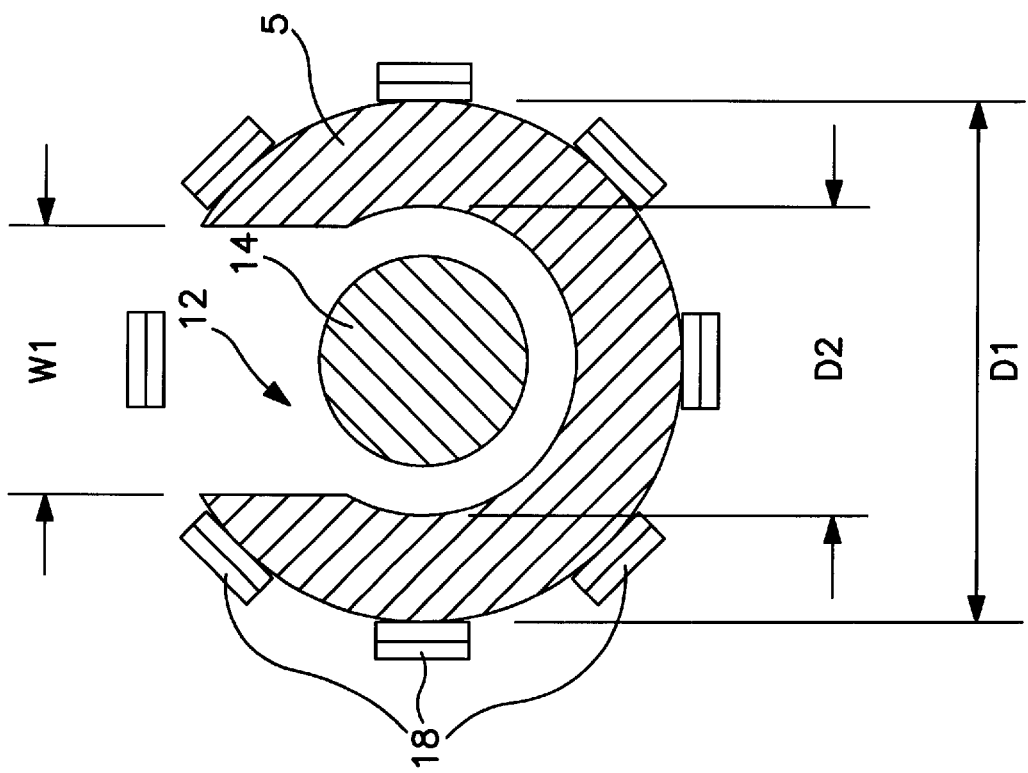

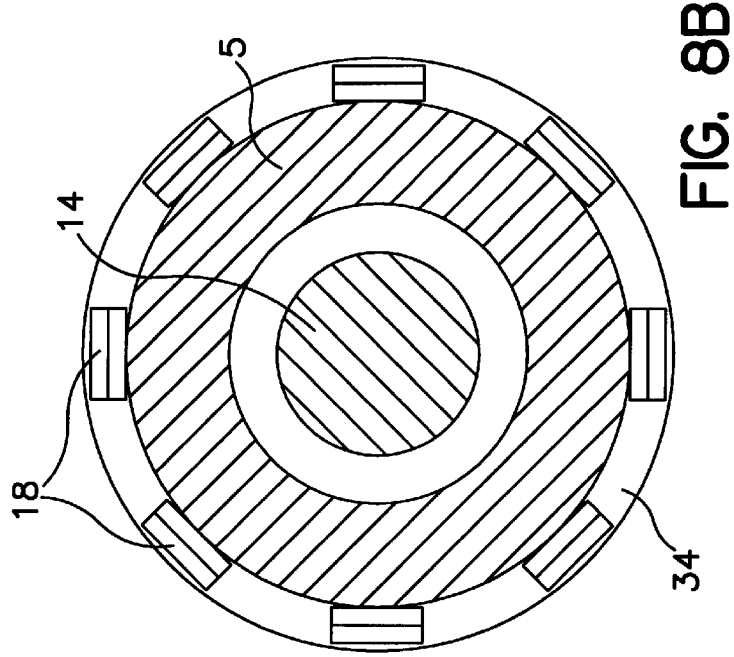
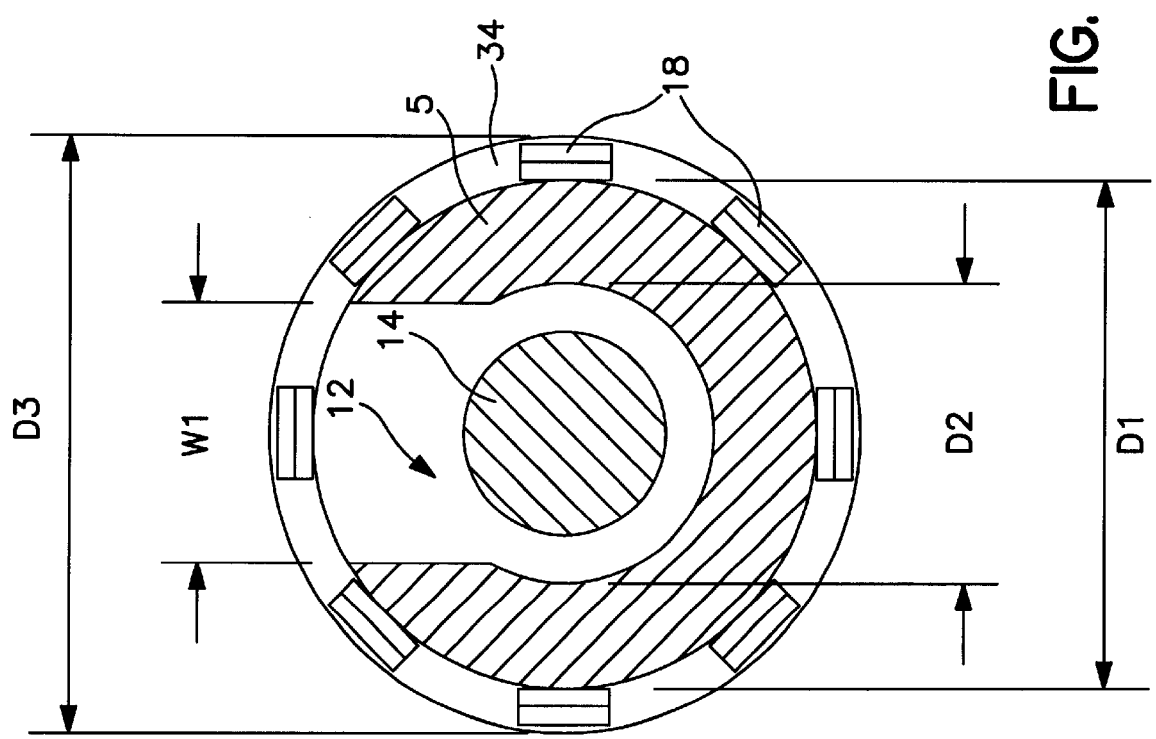
FIG. 8B
FIG. 8A

STEERABLE STYLET WITH ENHANCED TORSIONAL TRANSFER STRENGTH

CROSS REFERENCE TO CO-PENDING PATENT APPLICATION

Reference is made to commonly assigned U.S. patent application Ser. No. 09/659,797, filed on even date herewith by Gardeski et al. for a "Method and Apparatus for Deflecting a Screw-In Lead" which has related subject matter.

BACKGROUND OF THE INVENTION

The present invention relates to a wire guide or stylet assembly for the introduction of pacing or defibrillation leads and medical catheters to a desired site within a patient's body. Specifically, this invention relates to a steerable stylet assembly that imparts a desired dynamic curvature in the distal portion of a catheter or lead during its introduction. Such curvature is required to guide the catheter or lead through the patient's vascular system to a desired site within the heart. The present invention uses braided flat wire wrapped around a tubular member that allows the physician user to apply, via a handle equipped with a rotatable knob, enhanced torsional transfer strength to the stylet, making it easier to effect and maintain the desired curvature to the lead or catheter.

Generally speaking, pacing and defibrillation leads and catheters are highly flexible throughout their length so as to flex with the movement or contraction of the heart as well as other body or muscular movement. Such flexibility avoids the fracture of the lead body due to cumulative stress over time. As a result, however, implantable pacing and defibrillation leads and catheters are often too limp to be advanced through the venous system to a desired internal site within the patient's cardiovascular system. To assist in the placement of such devices, a thin stiffening stylet is inserted into the lumen of a lead or a steerable catheter to guide its passage through the venous system and ensure its proper placement at a desired site within the patient's heart or into a vessel, such as the coronary sinus. This thin wire stylet is inserted into the proximal opening of a lumen found in the lead connector pin, or in an accessory (secondary) lumen in the catheter, and extends down the length of the device. The stylet stiffens the entire assembly and may be bent at the distal end by a physician prior to placement within the lumen to provide a bend or curvature to the lead or catheter. The curved distal portion facilitates movement of the distal lead tip through the venous system and to the desired site within the patient's heart or other vessel within the cardiovascular system.

Many different types of stylets are available to aid in steering a catheter or lead. For example, some stylets must be provided with a desired shape prior to insertion of the stylet within the lead or catheter. From time to time, as a physician directs the distal tip of the lead or catheter to a desired location, it may be necessary to withdraw the stylet and insert a new stylet with a different curvature. This process of substituting a new and differently curved stylet may be used whenever a new obstacle to lead advancement is encountered.

This technique, however, has several drawbacks. For example, repeated insertion and withdrawal of the stylet may contaminate the lead lumen with blood. This is undesirable because drying blood may clot and jam the stylet within the lead, making stylet removal difficult and, perhaps, impossible, and thereby rendering the lead unusable. Moreover, the continued insertion, withdrawal, and substitution of other stylets is time consuming and has the potential for damaging the lead, the blood vessel, or both.

In order to avoid repeated withdrawal and reintroduction of stylets, other types of stylets have been proposed including those in U.S. Pat. No. 4,381,013 issued to Dutcher and U.S. Pat. No. 4,677,990 issued to Neubauer, both incorporated herein by reference in their entireties. A further example of a steerable stylet is disclosed in U.S. Pat. No. 4,846,175 assigned to Frimberger.

More recently, two alternative mechanisms have been proposed to make steerable stylets more useful. The first mechanism was proposed in U.S. Pat. No. 5,396,902 issued to Brennan, incorporated herein by reference in its entirety. The '902 patent discloses the use of a steerable stylet which can be deflected and curved within the lead during placement within the body via a manipulative handle coupled to the proximal end of a slotted, tubular member located at the distal end of the stylet via a pull (or tension) wire. Tension applied to the pull wire causes the distal end of the stylet to be deflected and curved to match the requirements of the physician during lead placement. The second mechanism appears in U.S. Pat. No. 6,027,462 issued to Greene, incorporated herein by reference in its entirety. The '462 patent discloses a handle which uses a rotating knob to effect the deflection of the tubular member, thereby providing curvature to the stylet and endocardial lead assembly.

The foregoing examples of stylet embodiments discuss the various mechanisms utilized to facilitate deflection of the distal end. To further facilitate tip deflection, material selection is important. In one embodiment, a stylet may be manufactured from a material having a very large elasticity. For example, a superelastic nickel-titanium alloy (nitinol) could be used for this purpose. By employing a material that is highly elastic, a large bending deflection may be sustained by the stylet tip without the tip breaking.

As discussed above, stylet tip deflection provides one mechanism of steering a lead or catheter through the vasculature during placement. Another mechanism involves the rotation of the distal end of the stylet. Once a curvature is introduced into the lead or catheter tip via the deflected stylet, it is often necessary to rotate the curved tip as it is guided into position. Optimally, rotation of the proximal end of a stylet by a predetermined amount will result in rotation of the distal end of the stylet by an equal amount. Although desirable, such one-to-one angular displacement throughout the length of a stylet is not achievable. All materials used to manufacture stylets and guidewires experience some twisting when a torque is applied to one end. This is particularly true of highly elastic metals such as superelastic nitinol generally desirable for use in achieving large stylet tip deflection. This is also particularly true of an elongated body having a small diameter such as a stylet or guidewire, since the torsional strength of a cylindrical body is proportional to the stylet or guidewire diameter to the third power. Thus, although the use of nitinol and other materials such as stainless steel results in a stylet with a highly-deflectable tip, this use has undesirable consequences such as providing a device that is relatively incapable of transferring rotational or angular displacement down the length of the stylet. The problem is exasperated by ever-smaller stylet and guidewire dimensions, as has been the recent trend. What is needed, therefore, is an improved system for transferring rotational force throughout the length of a stylet or guidewire, and for further improving the steerability of a lead or catheter body.

SUMMARY OF THE INVENTION

The present invention is directed to an improved version of a steerable guidewire or stylet that includes a braided structure that provides increased torsional strength to the stylet. The invention may be practiced with any type of stylet. In one embodiment, the stylet comprises an elongated tubular member having a pull wire residing within the tubular member. The distal end of the pull wire is anchored to the distal end of the tubular member. One or more apertures may be provided near the distal end of the tubular member located substantially within an elongated region lying parallel to the axis of the tubular member. These one or more apertures provide a preferential bending direction to the tubular member when tension is applied at a proximal end of the pull wire. In one embodiment, these one or more apertures comprise an elongated slot. The deflection capability of the stylet is enhanced by forming the tubular member from nitinol or another highly elastic metal.

As noted above, a braided structure holds the pull wire within the slotted tubular member. This braid may be formed of a metal such as stainless steel flat wire that optionally may be reinforced with polyimide. The braid may be provided along the entire length of the guidewire or stylet, or optionally may be utilized only at the distal tip. This braid greatly improves the torsional strength of the stylet so that rotational force applied at the proximal guidewire end may be transferred to the distal end. This increase in torsional strength is provided without any substantial decrease in the deflection capability of the distal tip of the stylet.

In one embodiment, the stylet or guidewire of the current invention utilizes a handle similar to that disclosed in the '462 patent. This handle is equipped with a rotatable knob and inner slider member. This knob and slider member may be slid distally relative to the handle to provide a mechanism for quickly forming a curve in the stylet or guidewire. This feature is particularly beneficial when a curve is needed only temporarily, for example in conjunction with deflecting the tip of the stylet, to facilitate entry into a desired blood vessel, such as the coronary sinus. Alternatively, the knob may be rotated to provide a larger deflection at the distal stylet tip. This handle provides a deflection mechanism having a minimum number of moving parts, and which is arranged to facilitate easy control of the degree of curvature displayed by the stylet or guidewire using only one hand.

Another embodiment of a handle that may be used with the current invention is shown and described in the Application Ser. No. 09/659,797 entitled "Method and Apparatus for Deflecting a Screw-In Lead", filed on even date herewith, and which is incorporated by reference in its entirety. This handle structure includes a detachable lead extension tool for coupling to a lead body, particularly for extendable-retractable leads. The disclosed system adapts the length of the lead to match a stylet, and further facilitating the ease with which deflection of a stylet tip may be accomplished.

BRIEF DESCRIPTION OF THE DRAWINGS

FIG. 1 is a diagram of an exemplary stylet as may be used by the current invention.

FIG. 2 is a diagram of a second embodiment of a stylet that may be employed with the current invention.

FIG. 5 is a perspective diagram illustrating braided structure provided over distal portion of the tubular member.

FIG. 6 is a perspective diagram illustrating braided structure provided over the length of the outer member.

FIG. 7A is a cross-sectional diagram of the stylet of the current invention shown at Section A—A of FIG. 6, and having a braided structure formed from a flat metal.

FIG. 7B is a cross-sectional diagram of the stylet of the current invention shown at Section B—B of FIG. 6, and having a braided structure formed from a flat metal.

FIG. 8A is a cross-sectional diagram of the stylet of the current invention shown at Section A—A of FIG. 6, and having a braided structure formed from a flat metal reinforced with a polyimide.

FIG. 8B is a cross-sectional diagram of the stylet of the current invention shown at Section B—B of FIG. 6, and having a braided structure formed from a flat metal reinforced with a polyimide.

DETAILED DESCRIPTION OF THE DRAWINGS

Figure 3:
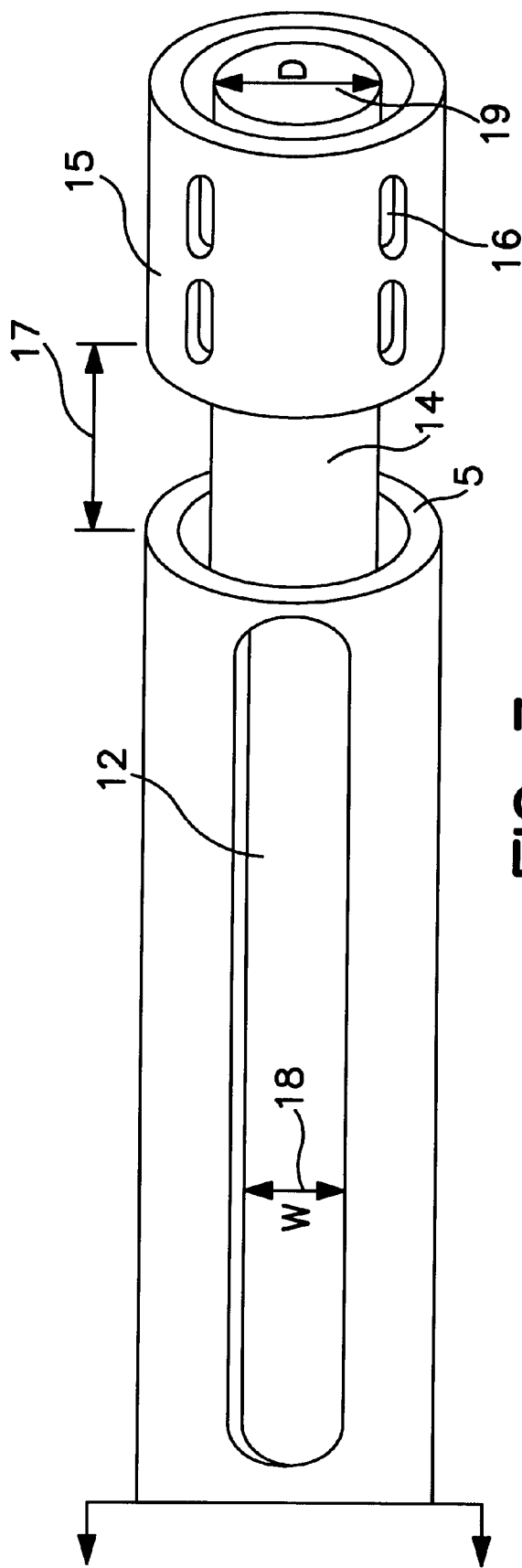
FIG. 3 is an exploded perspective diagram of the distal tip of the stylet shown in either FIGS. 1 or 2.

FIG. 1 is a diagram of an exemplary stylet 2 as may be employed by the current invention. The stylet includes a handle 4, which may be one of the embodiments described below, or any other type of handle. Stylet 2 includes an outer member 5 which may be tubular, and which is comprised of proximal portion 6 and a distal portion 8 joined at seam 10. Proximal portion 6 may be formed of a first metal material such as stainless steel or a polyimide. Distal portion 8 may be formed of a second material having superior elastic properties such a superelastic nickel titanium alloy (nitinol) or another similar metal. By using a superelastic alloy to form the distal tip, the tip may be subjected to a large deflection force without breaking.

In the embodiment of FIG. 1, a superelastic material is used only at the distal portion 8 where the majority of stylet deflection will occur. A different material is employed to form the rest of the stylet body. This design choice has the advantage of minimizing the effects of the poor torsional strength exhibited by the superelastic material at the distal tip. Since this type of material does not transfer rotational forces efficiently, it may be desirable to use a different type of material such as stainless steel over a large proximal portion of the stylet. In addition to exhibiting a higher torsional strength, a stiffer material such as stainless steel is more "pushable", making the stylet less difficult to push through the vasculature.

Distal portion 8 includes slot 12. This slot is used to provide a preferred bending direction for the distal tip portion 8 of stylet 2. When deflected, the distal tip of the stylet will bend in the direction of the slot, such that the slotted edge defines the inner curve of the deflected distal tip. Other types of stylets may be used with the current invention, including stylets having multiple apertures arranged along one side of the stylet body to define the preferential bending direction.

The stylet of FIG. 1 further includes pull wire 14 inside of outer member 5. This pull wire extends the full length of the stylet, and is connected to handle 4. Embodiments of this handle interconnection are discussed below. The pull wire may be formed of stainless steel, nitinol, or other suitable material such as a Dacron, ultra-high molecular weight polyethylene (UHMWPE), or polyetheretherketone (PEEK) monofilament. The pull wire is also attached to the distal end of outer member 5 as with crimping sleeve 15 which may be formed of a stainless that is crimped to the distal end of outer member 5. Tension applied to pull wire at the handle 4 results in deflection of outer member 5 in the area of slot 12, as discussed above.

FIG. 2 is a diagram of a second embodiment of a stylet that may be employed with the current invention. This stylet 2A includes many of the elements shown in FIG. 1, including handle 4, outer member 5, slot 12, pull wire 14, and crimping sleeve 15. However, outer member 5 of stylet 2A does not include distal and proximal sections joined at a seam such as that shown as seam 10 in FIG. 1. In this embodiment, both distal and proximal ends of outer member 5 are formed of the same material which may be a superelastic material such as nitinol, or may be a different material such as stainless steel or a polyimide.

The embodiment of FIG. 2 has the advantage as compared to that of FIG. 1 of not including seam 10 as shown in FIG. 1. Formation of this seam requires a more complicated manufacturing process than that required to form a stylet of only one material. However, this embodiment does not provide the advantage of having a first material with an increased torsional strength at the proximal end, and having a second material having an increased deflection capability at the distal end.

FIG. 3 is an exploded perspective diagram of the distal tip of the stylet shown in either FIGS. 1 or 2. This figure includes outer member 5, pull wire 14, crimping sleeve 15, and slot 12. In one embodiment, the width W of slot 12 is greater than the diameter D of pull wire 14. This prevents the pull wire from binding in slot 12. In other embodiments, the width W of slot 12 may be less than diameter D of pull wire 14.

FIG. 3 further shows crimping indentations 16 included in crimping sleeve 15 to couple crimping sleeve 15 to pull wire 14. The gap 17 between crimping sleeve 15 and outer member 5 is relatively small so that tension exerted on the proximal end of pull wire 14 causes crimping sleeve 15 to come in contact with outer member 5, thereby exerting a deflection force on outer member 5.

As discussed above, many materials do not exhibit good torsional strength. This is particularly true of a superelastic metal such as nitinol. To increase the torsional strength of the outer member 5, a braided structure may be used to form a sheath around tube. The braided structure is made from a material such as stainless steel Type 304 with an elastic modulus higher than the slotted outer member. The braid arrangement provides for ease in bending (flexibility)while the higher elastic modulus provides for optimal torsional strength.

Figure 4A:
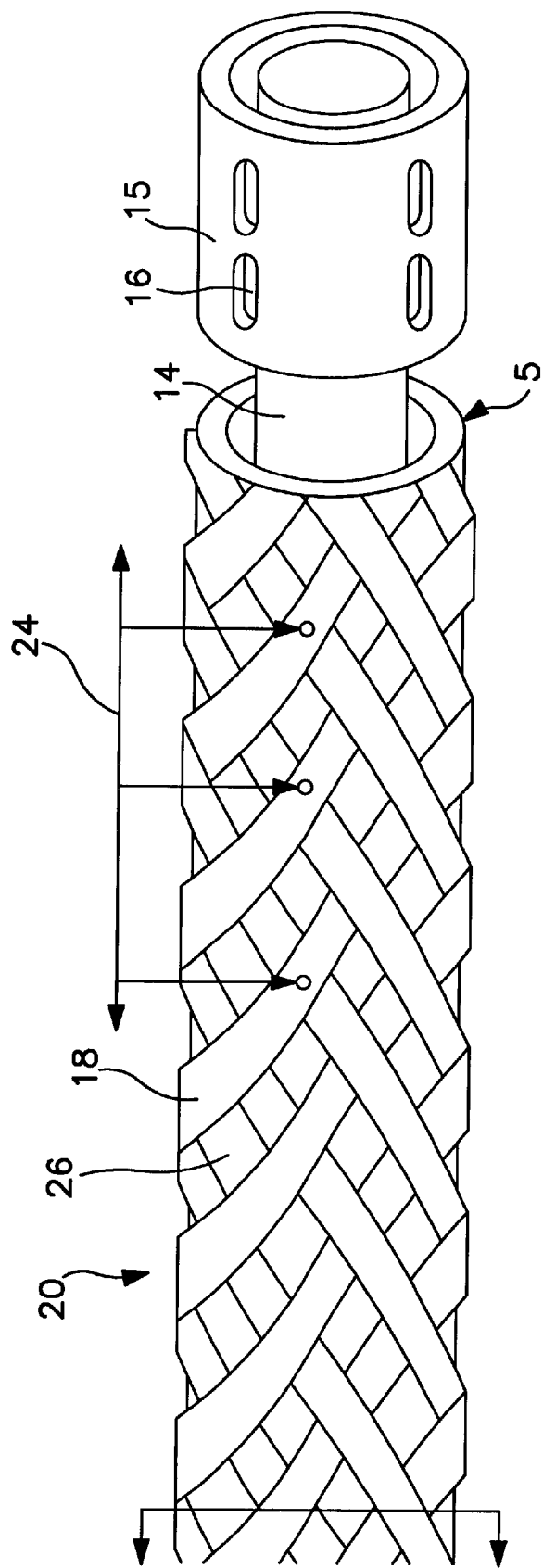
FIG. 4A is a perspective diagram of a distal tip portion of the stylet including braided structure.

FIG. 4A is a perspective diagram of a distal tip portion of stylet 2 or 2A including braided structure 18. The braided structure serves to hold pull wire 14 within slotted outer member 5 when tension is applied at the proximal end of the pull wire. Additionally, the braided structure greatly improves the torsional strength of the stylet so that rotational force applied at the proximal end may be transferred to the distal end. This increase in torsional strength is provided without any substantial decrease in the deflection capability of the distal tip of the stylet. Braided structure 18 is coupled to outer member 5 in at least one location. This coupling may be accomplished by using a resistance or laser welding process. Alternatively, braided structure may be soldered, for example, by using a silver solder. In yet another embodiment, the coupling may be performed using a brazing process, or by using crimping rings. An adhesive bonding process may also be used to couple the braided structure to the outer member 5.

After braided structure 18 is coupled to the outer member 5, both the braided structure and the outer member 5 may be drawn through a die to remove slack and to perform final sizing.

Figure 4B:
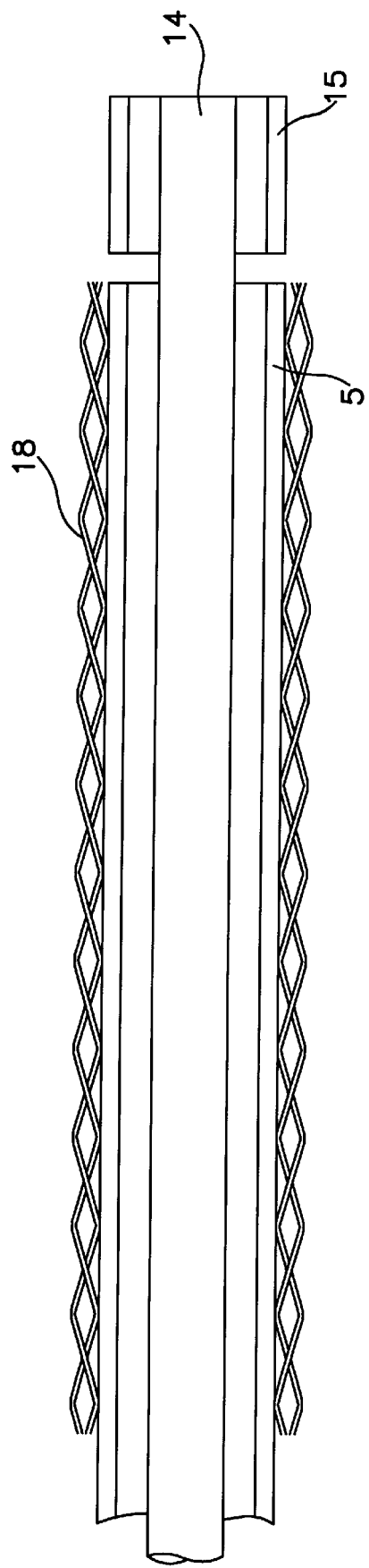
FIG. 4B is a longitudinal cross-sectional view of distal tip portion of stylet, including the braided structure.

FIG. 4B is a longitudinal cross-sectional view of distal tip portion of stylet 2 or 2A, including braided structure 18.

Braided structure may be formed of a variety of materials. In one embodiment, the braid may be formed of a metal such as stainless steel flat wire alone, or a stainless steel flat wire that has been reinforced with polyimide. For example, stainless steel flat wire Type T304V may be used. Preferably, the metal utilized for the braid has an Ultimate Tensile Strength (UTS) in the range of 200,000 to 350,000 lbs/in$^2$.

Another material that may be used for the braid is a precipitation-hardening stainless steel such as PH17-7 or Custom 450 or 455. This type of material is relatively soft in the annealed condition, and therefore is easier to braid and to terminate than high temper stainless steel type 304 ribbon wire. For example, Custom 450 can be readily terminated by welding the wires where the wires cross (pic crossings). The braid structure can then be age-hardened in a single heat treatment to achieve substantially higher yield strengths than type 304 stainless steel.

Yet another material that may be utilized to form the braid is a molybdenum having a modulus of approximately 50,000,000 lbs/in$^2$. Molybdenum is significantly stronger than stainless steel, which has a modulus of approximately 29,000,000 lbs/in$^2$. Molybdenum is routinely rolled into flat stock while maintaining a good surface finish.

Another alternative embodiment is provided by using a round wire instead of a ribbon wire to form the braid. This embodiment is suitable for steerable stylets having a diameter between 0.020 and 0.025 inches. Use of a round wire has the disadvantage of increasing the diameter of the stylet. However, in this embodiment, the braid may be more flexible since there is less wire-to-wire surface contact at the wire pic-crossing.

The braided structure may be woven in many different types of patterns. FIG. 4 illustrates a "two-over, two-under" braid pattern.

In one embodiment, the braided structure is woven from ribbon wire that is 0.0005 thick and 0.0025 inches wide, and has a pic count between 100 and 160. Pic count is a measurement of the tightness of the weave of the braided structure. Pic count is calculated by counting the number of times strands in the first direction and strands in a second direction cross within a one-inch line drawn longitudinally along the stylet. For example, assuming arrow 24 measures a one-inch segment of the stylet, the pic count would be "three". In the alternative, tightness of the weave may be described using braid angle, which is the included angle measured in the longitudinal direction between two crossing wires.

It is important to maintain a pic count that is not so great that deflection capability is impacted. For instance, FIG. 4 illustrates a weave in which spaces, such as space 26, remain between adjacent strands such as space 26. Such spaces are necessary to allow the strands to move slightly when distal tip of outer member 5 is deflected. If the strands are woven so tightly that no spaces remain, more force must be applied to pull wire 14 to achieve tip deflection. This makes the stylet more difficult to use.

Braided metal of the type used to form the current invention is available in many different dimensions. According to one embodiment of the invention, a flat braid of T304V stainless steel having a thickness of 0.0005 inches, and a width of 0.0025 inches may be used. In this embodiment, a braided structure having a pick count of 124 picks per inch may be used. In another embodiment, a flat braid of Type T304V stainless steel having a thickness of 0.0007 inches, and a width of 0.005 inches may be used. In this embodiment, a braided structure having a pick count of 50 picks per inch may be used. Preferably, the ribbon wire has a thickness less than 0.0010 inches, with the width being limited by the braiding process. Generally, a width greater than 0.010 inches becomes too difficult to braid at these diameters.

The current invention provides a stylet with a minimum diameter. This is because a very small outer member 5 can be utilized while still maintaining a stylet with acceptable torsional strength. In one embodiment of the invention, the stylet, including the braided structure 18, has a diameter that is smaller than 0.025 inches, and is generally between 0.015 and 0.025 inches. Of course, larger stylets may also take advantage of the current invention to improve torsional rigidity.

In one embodiment of the invention, braided structure may extend from handle 4 to the distal tip of outer member 5. In another embodiment, braided structure may be provided over only distal portion 8 of outer member 5, as shown in FIG. 1. If the braided structure is provided over the entire length of outer member 5, the braided structure does not require termination at an intermediate location on outer member 5. This is desirable since this type of termination requires a more complex manufacturing process to achieve. Additionally, the full-length braided structure will provide a combined increase in bending flexibility along with an increased torsional strength over the entire length of outer member 5. Thus is advantageous regardless of whether stainless steel, nitinol, or a polyimide is used at the proximal end, or throughout the entire length, of outer member 5.

FIG. 5 is a perspective diagram illustrating braided structure 18 provided over distal portion 8 of outer member 5.

FIG. 6 is a perspective diagram illustrating braided structure 18 provided over the entire length of outer member 5.

As noted above, in one embodiment, braided structure 18 is formed of a flat metal wire structure. In another embodiment, the braided structure may be reinforced with a high-performance polyimide such as one commercially available from Phelps Dodge, Inc. of Trenton Ga., or a rigid polyamide (nylon) material. For example, a reinforced braided structure may be formed by dipping a tubular core in a polyimide. After the polyimide has cured, a braided structure is woven around the dipped core. Finally, the dipped core and braided structure are re-dipped in the polyimide. After the second coating of polyimide has set, the core structure is removed. The braided tubular structure slides over the stylet outer member 5 and is adhesively bonded to stylet outer member 5 with epoxy adhesive. The above dipping process is commonly performed in a reel-to-reel continuous process.

FIG. 7A is a cross-sectional diagram of the stylet of the current invention at location A of FIG. 6. The cross-section shows slot 12, and braided structure 18 at the braid intersection points. In one embodiment, the outer diameter D1 of outer member 5 is 0.0136 inches, the inner diameter D2 of outer member 5 is 0.0080 inches, and the slot width W1 is 0.0070. The ribbon wire included in braided structure 18 may have a thickness of 0.0005 inches, and a width of 0.0025 inches.

FIG. 7B is a cross-sectional diagram of the stylet of the current invention at location B of FIG. 6.

FIG. 8A is a cross-sectional diagram of the stylet of the current invention at location A of FIG. 6, and having a braided structure formed from a flat metal that is reinforced with a polyimide sheath 34. In one embodiment, the stylet has dimensions that are similar to that discussed above in reference to FIG. 7. In this embodiment, the diameter D3 of the polyimide sheath 34 is 0.0160 inches.

FIG. 8B is a cross-sectional diagram of the stylet of the current invention at location B of FIG. 6, and having a braided structure formed from a flat metal that is reinforced with a polyimide sheath 34.

In the foregoing embodiments, braided structure 18 is shown external to outer member 5. In an alternative embodiment, braided structure may be coupled to the internal surface of outer member 18. This embodiment is particularly beneficial if the diameter of the pull wire 14 is equal to or greater than slot width W1 (FIG. 8A).

Figure 8C:
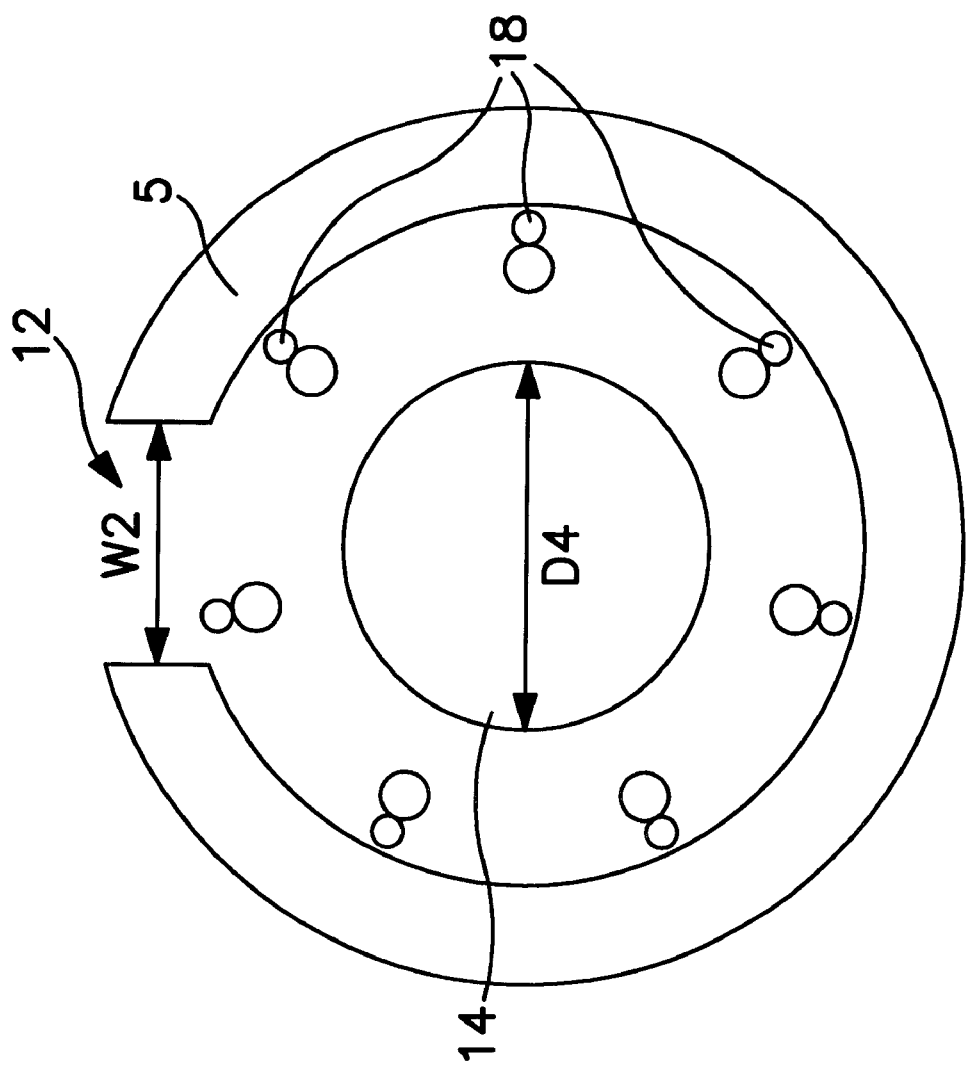
FIG. 8C is a cross-section diagram of the stylet of the current invention shown at Section A—A of FIG. 6 and having a braided structure located within the interior space of the stylet outer member.

FIG. 8C is a cross-section diagram of the stylet of the current invention having braided structure located within the interior space of outer member 5. This diagram further shows slot 12 having a smaller width W2 than the diameter D4 of pull wire 14, although this is not a requirement. Braided structure 18 is located within outer member 5. This embodiment further shows round wire being included in braided structure 18, although ribbon wire may be used in the alternative. Braided structure may also include a polyimide sheath, as shown in FIGS. 8A and 8B.

As discussed above, the current invention allows rotational force applied at a proximal end of a tubular structure to be transferred more efficiently to the distal end of the tubular structure.

Figure 9:
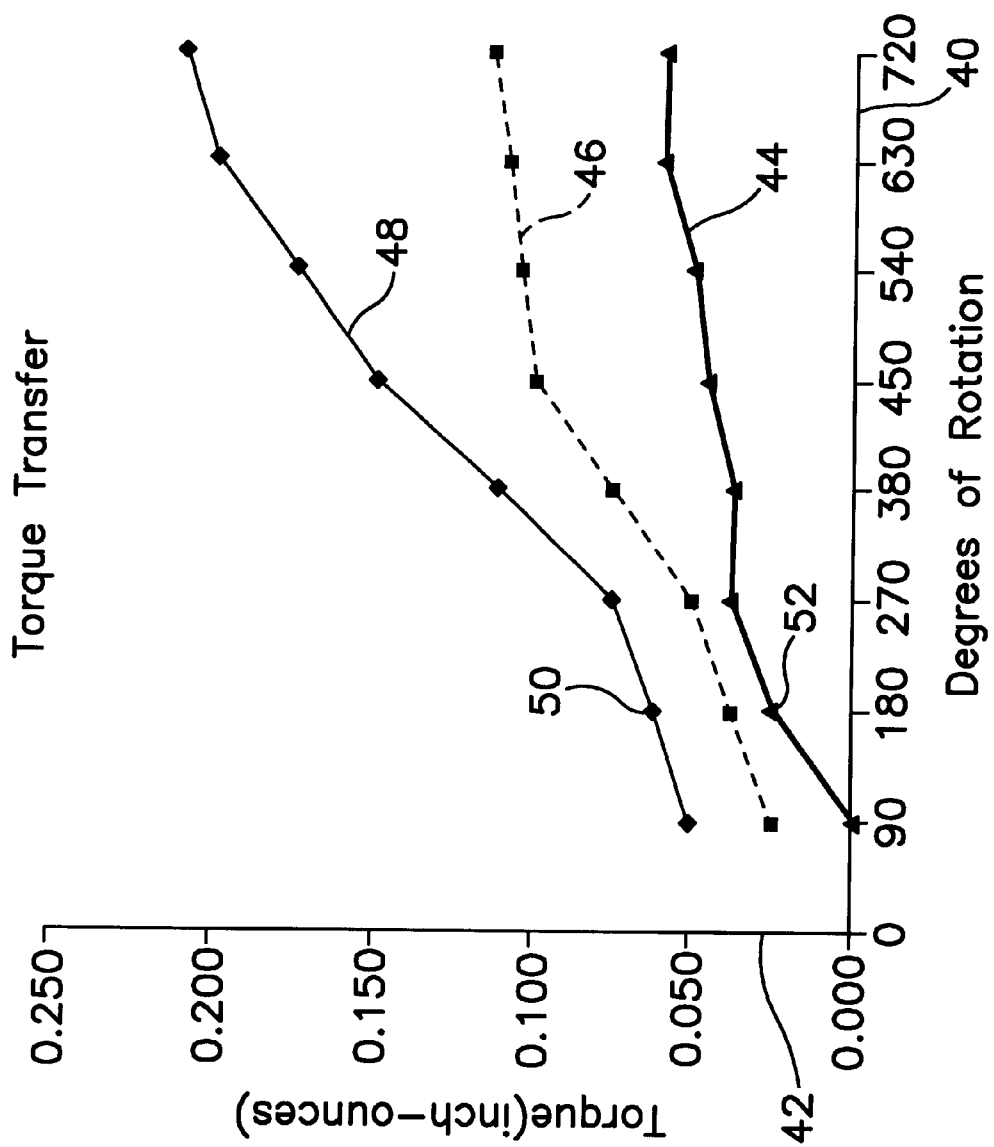
FIG. 9 is a diagram illustrating the improved torsional strength provided by the braided structure of the current invention.

FIG. 9 is a diagram illustrating the improved torsional strength provided by the braided structure of the current invention. The X axis 40 represents degrees of rotation of the proximal end of a stylet. The Y axis 42 represents the amount of torque, in inch-ounces, transferred throughout the length of the stylet. Plot 44 illustrates the performance of a stylet having a nitinol outer member 5 with a polyimide sleeve. Plot 46 illustrates the performance of a stylet having a nitinol outer member 5 surrounded by a braided structure 18 formed of a stainless steel flat wire braid reinforced with a polyimide. Plot 48 illustrates the performance of a stylet having a nitinol outer member 5 surrounded by a braided structure 18 formed of a stainless steel flat wire braid. As shown by points 50 and 52 of the graph, when a proximal end of a stylet is rotated through 180 degrees, more than twice as much rotational force is transferred per inch of a stylet having a braided stainless steel structure as compared to a stylet not having such a structure, respectively.

As discussed above, the current invention may be practiced with any type of stylet, including a stylet without a pull wire structure. However, in a preferred embodiment, the current invention is used with a stylet have a pull wire to deflect the distal tip. Many different mechanisms are available to achieve this deflection. According to one embodiment, a handle having a rotation knob may be utilized to apply tension to the tip structure, thereby causing deflection.

Deflectable Stylet Systems for Use with a Braided Stylet Structure

Figure 10:
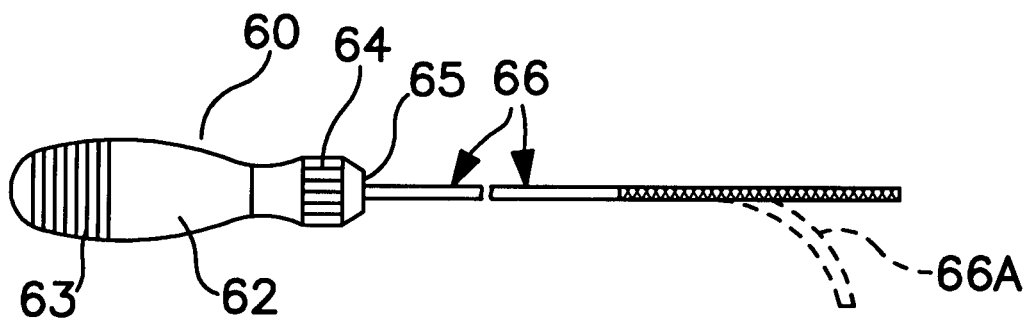
FIG. 10 is a plan view of a deflectable stylet with a braided structure according to the current invention, and further including a rotatable knob handle that may be used to deflect the distal tip of the stylet.

FIG. 10 is a plan view of a deflectable stylet with a braided structure according to the current invention, and further including a rotatable knob handle that may be used to deflect the distal tip of the stylet. Deflectable stylet 66 is shown with a handle 60 provided with a main handle portion 62 and a spinner or rotatable knob portion 64. A distal portion of deflectable stylet 66 is shown with a braided structure 65, although it will be understood that more, or all, of the deflectable stylet 66 may be braided. The main handle portion 62 may be provided with circumferential grooving 63 at its proximal end, while the spinner or rotatable knob 64 may be provided with external ribbing or knurling as illustrated. The deflectable stylet 66 exits from a proximal recess 65, within the spinner or rotatable knob 64. The rotation of spinner or knob 64 or distal advancement of knob 64 relative to the handle 62 causes deflection of the distal portion of stylet 66 to a curved configuration as illustrated at 66A.

Deflectable stylet 66 may take the form of any known deflectable stylet employing an outer member and an inner tension or pull wire which, when tension is applied to the distal tip of deflectable stylet 66, causes the tip of the stylet to curve 66A. Alternatively, deflectable stylet 66 may be replaced by a deflectable guidewire, for example, as disclosed in U.S. Pat. No. 4,815,478 issued to Buchbinder, incorporated herein by reference in its entirety. In all of these various guidewires and stylets, the basic structure of the deflectable stylet or guidewire consists of an outer member for steerable guidewire that displays a generally straight configuration in the relaxed condition. The structure further includes an internal pull or tension wire coupled to the distal portion of the guidewire or stylet, and arranged such that, upon application of tension to the distal tip of the guidewire or stylet, the distal portion of the guidewire or stylet exhibits a curved configuration.

Figure 11:
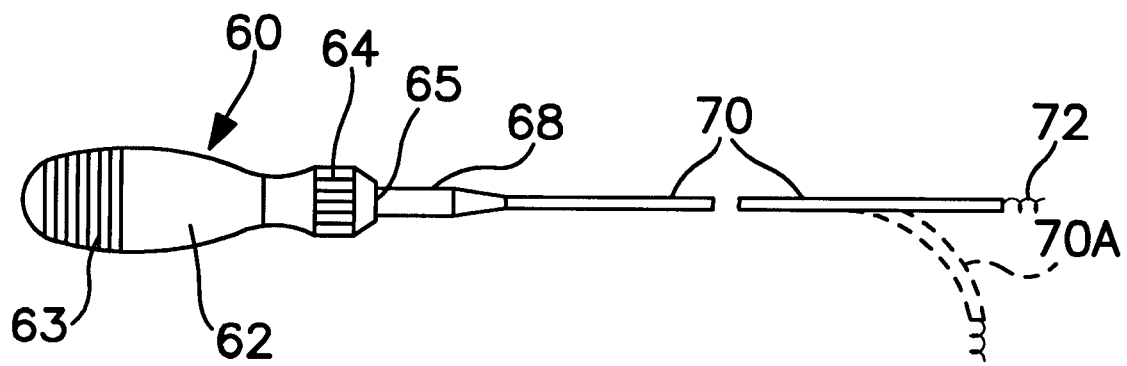
FIG. 11 is a plan view of the deflectable stylet of FIG. 1 inserted into a cardiac pacing lead.

FIG. 11 is a plan view of the deflectable stylet of FIG. 1 inserted into a cardiac pacing lead 70. Cardiac pacing lead 70 has a connector assembly 68 located at its proximal end, which typically carries a connector pin as is typical of cardiac pacing leads. For example, the distal portion of the connector assembly 68 may correspond to the IS-1 connector standard as disclosed in U.S. Pat. No. 4,922,607 issued to Doan et al., also incorporated herein by reference in its entirety. However, other connector configurations, such as disclosed in U.S. Pat. No. 4,488,561 issued to Doring or U.S. Pat. No. 4,572,605 issued to Hess et al., both also incorporated herein by reference in their entireties, may also be employed. At the distal end of pacing lead 70 is located an electrode such as a fixed helical electrode 72, which was disclosed in U.S. Pat. No. 5,473,812 issued to Morris et al. and incorporated herein by reference in its entirety, which is screwed into heart tissue in order to stimulate the heart. However, any other type of known pacing electrode may be substituted for electrode 72, or alternatively other types of electrodes such as cardioversion or defibrillation electrodes may be added to, or substituted for, electrode 72. Examples of pacing and cardioversion electrodes generally that might be employed in conjunction with a lead to be deflected by the deflectable stylet of the present invention include those described in U.S. Pat. No. 5,282,844 issued to Stokes et al., U.S. Pat. No. 4,506,680 issued to Stokes, U.S. Pat. No. 4,033,357 issued to Helland et al., U.S. Pat. No. 4,727,877 issued to Kallok, U.S. Pat. No. 5,115,818 issued to Holleman et al. and U.S. Pat. No. 5,728,149 issued to Laske et al., all also incorporated herein by reference in their entireties.

Figure 12:
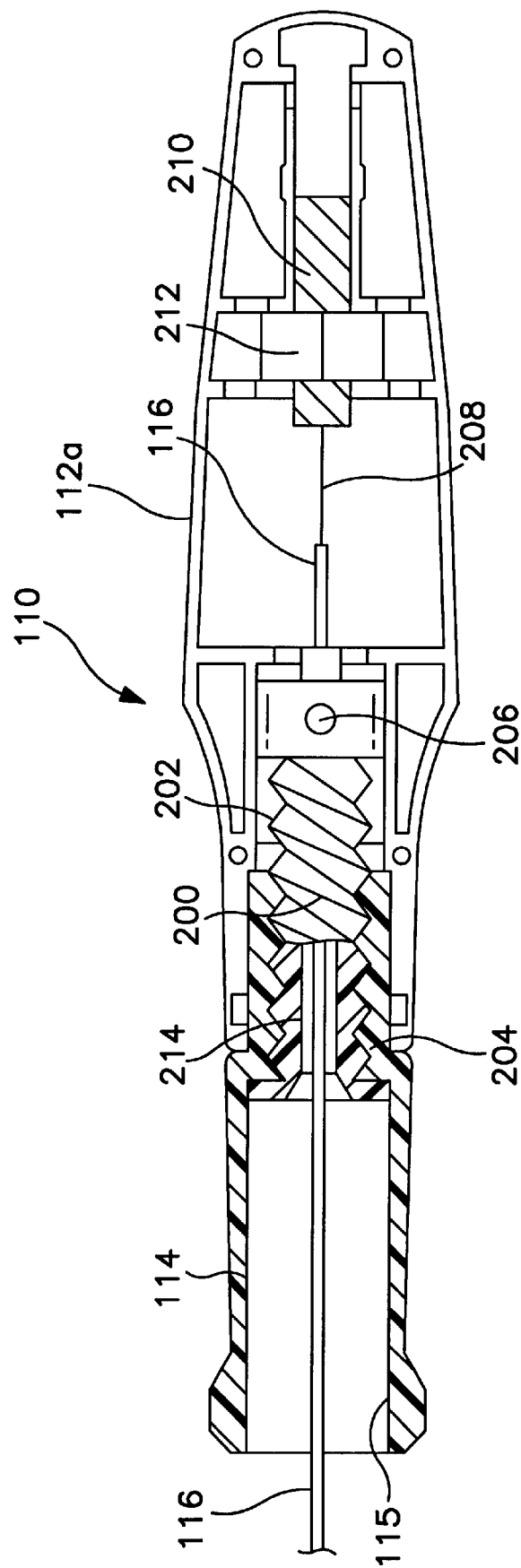
FIG. 12 is a cutaway view of one embodiment of stylet system that may be used with the current invention.

FIG. 12 is a cutaway view of one embodiment of stylet system that may be used with the current invention. This embodiment is similar to that disclosed in U.S. Pat. No. 6,027,462 issued to Greene, incorporated herein by reference in its entirety. The system is shown with a partially disassembled handle assembly 110. The handle 112 is fabricated of two molded plastic parts, joined together essentially along a longitudinal line extending the length of the handle. One of the two handle halves 112A is illustrated in conjunction with the knob or spinner 114, showing cross-section and the internal slider 200, not visible in the previous illustrations. The internal, distally facing recess 115 in knob 14 is visible in this view, and is sized to be of sufficient length that it inherently serves as a strain relief to the deflectable stylet 116, preventing kinking or bending of the stylet at the point it exits the slider 200. Recess 115 also assists the physician in repositioning his hand when moving between proximal and distal positions relative to the handle, in that the portion of the connector assembly distal to the connector pin is immediately adjacent the distal end of the knob.

The slider 200 generally takes the form of a rod provided with external threading 202 which engages internal threading 204 within knob 114. At the proximal end of the slider 200 is a collar 206 that engages corresponding grooves in the molded handle halves, not visible in this drawing, to prevent rotation of the slider 200 relative to the handle. Thus, rotation of the knob 114 relative to the handle causes longitudinal movement, but not rotational movement of the slider 200. The outer tube of deflectable stylet 116 is mechanically coupled to the slider 200, while the tension wire 208 within the stylet 116 is anchored to the handle. Thus, on distal movement of the slider 200 relative to the handle 112A, the outer tube of the stylet is moved with respect to the tension wire 208, causing tension wire 208 to apply tension to the tip of the stylet and deflecting it, in the manner described above in the various cited patents pertaining to deflectable stylets. Tension wire 208 is anchored to a threaded rod 210 which is adjusted longitudinally by means of a hex nut 212, which is fixedly mounted in the handle.

As illustrated, the knob 114 and the slider 200 may be slid distally with respect to the handle as a unit, providing an alternative mechanism for applying tension to tension wire 208 and deflecting stylet 216. Deflection of the stylet by this mechanism is convenient in the case in which the physician wants to only very briefly and very quickly induce a curve to facilitate entry of the lead into a desired location, for example, into the coronary sinus or for navigating the lead through the vena cava and through the tricuspid valve.

In the embodiment illustrated, the slider is provided with an internal bore 214 which may receive the connector pin of an implantable lead. In this case, the bore 214 should be of larger diameter than the connector pin, so that the lead may be rotated with respect to the stylet 216. Alternatively, the bore 214 may be omitted, with the connector pin simply lying adjacent the distal end of the slider 200.

Figure 13:
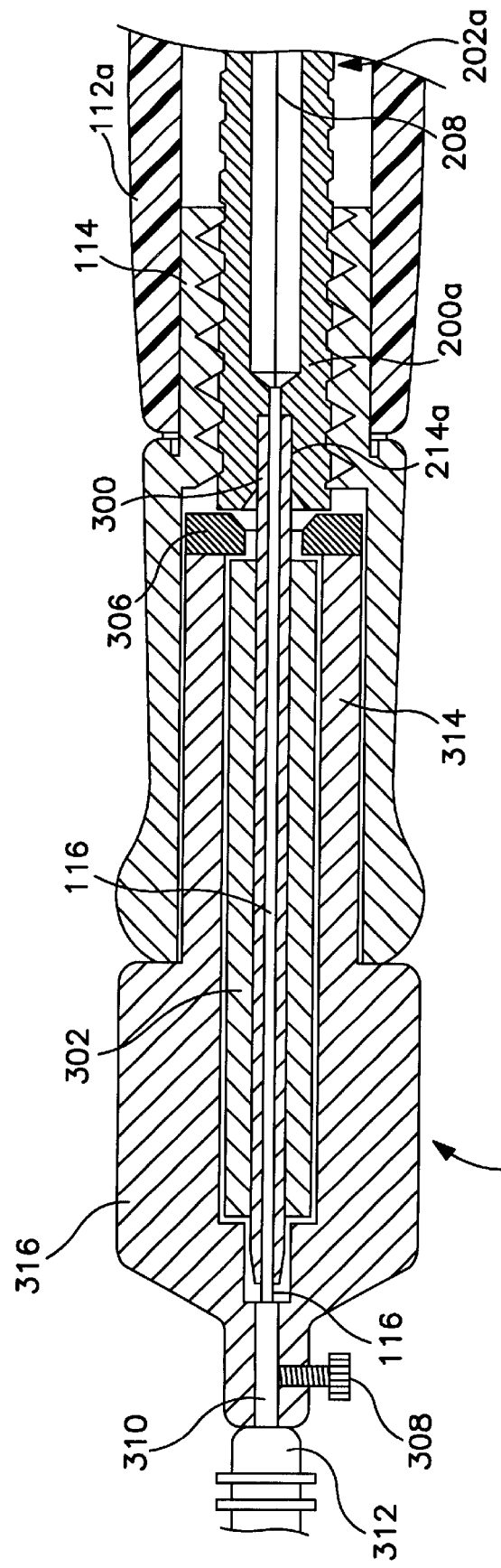
FIG. 13 illustrates a cutaway view through the distal portion of a deflectable stylet handle in conjunction with an attachment according to the invention, to which the connector pin of a lead of the type having a fixation helix is attached.

FIG. 13 illustrates a cutaway view through the distal portion of a deflectable stylet handle in conjunction with an attachment according to the invention, to which the connector pin of a lead of the type having a fixation helix is attached. As illustrated, the deflectable stylet control handle corresponds generally to that described in the above cited Greene et al patent and as illustrated in FIG. 12. Handle 112A, knob or spinner 114, deflectable stylet 116 and tension wire 208 correspond to identically numbered components as illustrated in FIG. 12. Slider 200A of this embodiment corresponds generally to slider 200, with the exception that the outwardly extending screw threads 202A are somewhat reduced in height from those employed in slider 200 (FIG. 12). Operation of the deflectable stylet handle in and of itself is identical to that described above in conjunction with FIG. 12.

Also illustrated is an attachment 304 according to the present invention, mounted to the stylet handle. Attachment 304 includes a generally cylindrical knob 316 from which a generally tubular member 314 extends proximally. Tubular member 314 is rotatably mounted within the distal facing recess of knob or spinner 114 and is also slidable longitudinally within that recess. At the distal end of the attachment 304 is a distally facing bore in which the connector pin 310 of a pacing lead 312 is inserted and is retained by screw 308. Lead 312 should be understood to be a lead of the type having a fixation helix, wherein the fixation helix is advanced by rotation of connector pin 310, either to rotate the lead body or to rotate the helix relative to the lead body.

Located within the proximally extending tubular member 314 of attachment 304 is a bushing 302, which surrounds a tubular pin 300 that is in turn mounted around deflectable stylet 116. Bushing 302 is adhesively or otherwise bonded to the interior of the tubular member 314, and is free to rotate with respect to tubular pin 300. Tubular pin 300 is mounted within recess 214A, in the distal end of slider 200A, and is retained therein frictionally, by adhesive or otherwise. Plug 306 is mounted to the proximal end of the tubular member 314. As discussed below, the provision of pin 300 allows for an increase in the range of available longitudinal movement of attachment 304 relative to a deflectable stylet handle, and thus an improvement in the degree of adjustability of the assembly for use both in conjunction with leads of different lengths and in order to adjust the position of the stylet 116 within the body of lead 312.

Figure 14:
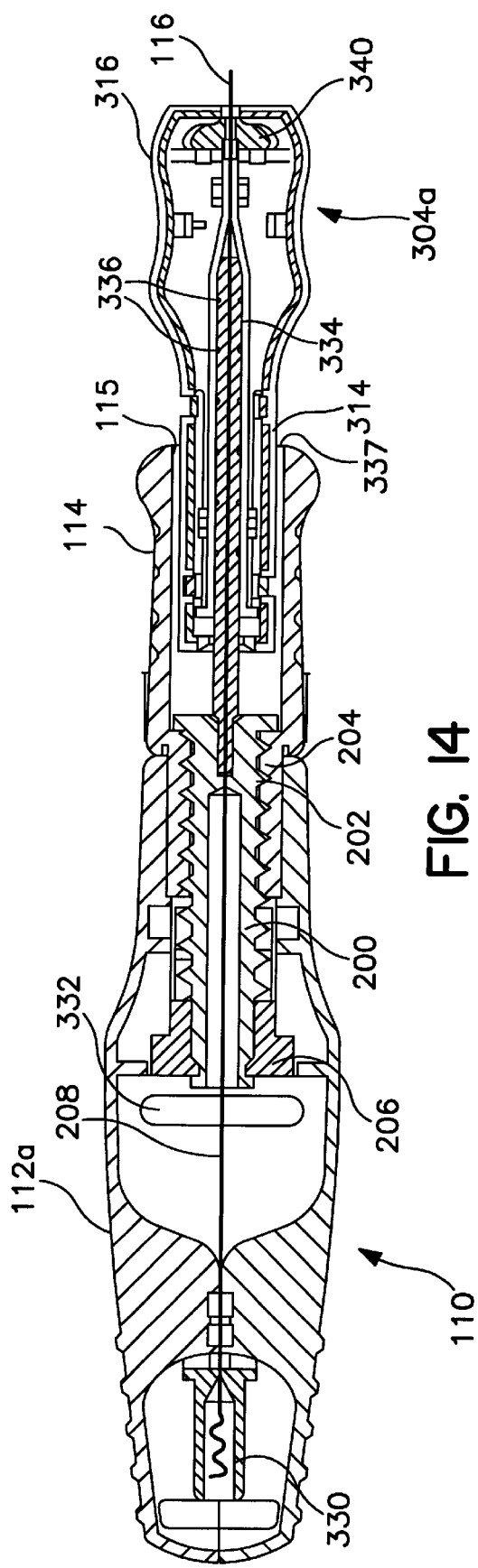
FIG. 14 is a cutaway view of another embodiment of handle assembly and attachment, as illustrated in the figures discussed above.

FIG. 14 is a cutaway view of another embodiment of handle assembly and attachment 304, and is similar to that disclosed in U.S. patent application Ser. No. 09/659,797, filed on even date herewith by Gardeski et al. for a "Method and Apparatus for Deflecting a Screw-In Lead" incorporated herein by reference in its entirety.

In this Figure, all components corresponding to those in FIGS. 12 and 13 are labeled with the same reference numbers as used in the previous FIGS. 12 and 13 for ease of reference. As in the embodiments discussed above, this embodiment includes a handle fabricated of two molded plastic parts, joined together essentially along a longitudinal line extending the length of the handle. One of the two handle halves shown as 112A is illustrated in conjunction with the knob or spinner 114, shown in cross-section, and the internal slider 200, not visible in the previous illustrations.

The embodiment of the handle shown in FIG. 14, which is similar to that shown in previous FIGS. 12 and 13, includes another implementation of the attachment. As in the embodiments discussed above, the attachment is fabricated of two molded plastic parts, joined together essentially along a longitudinal line extending the length of the handle, with the half of the attachment 304a being shown in FIG. 14. In a manner similar to that discussed above in reference to FIG. 13, this attachment includes a generally cylindrical knob 316 from which a generally tubular member 314 extends proximally. Tubular member 314 is rotatably mounted within the distal facing recess of knob or spinner 114 and is also slidable longitudinally within that recess. In this embodiment, tubular member 314 includes a coupling mechanism (not shown in FIG. 6) to be described further below. This coupling mechanism is adapted to be rigidly positioned with respect to any of the notches 336 included within pin 334. Thus, attachment 304a may be rigidly re-positioned at predetermined intervals along at least a predetermined portion of the length of pin 334.

In this embodiment, attachment 304a further includes a lead attachment mechanism that uses a pushbutton clevis to fix the lead pin to attachment 304a. FIG. 14 illustrates a cross-section of this pushbutton 340 that couples the connector pin 310 of a pacing lead 312 to the attachment, and which is discussed further below. This is an alternative coupling mechanism to screw 308 of FIG. 13. The embodiment of FIG. 14 provides the advantage of requiring only a single, one-handed motion to engage and disengage the coupling mechanism as compared to the screw 308 of FIG. 13.

Figure 15:
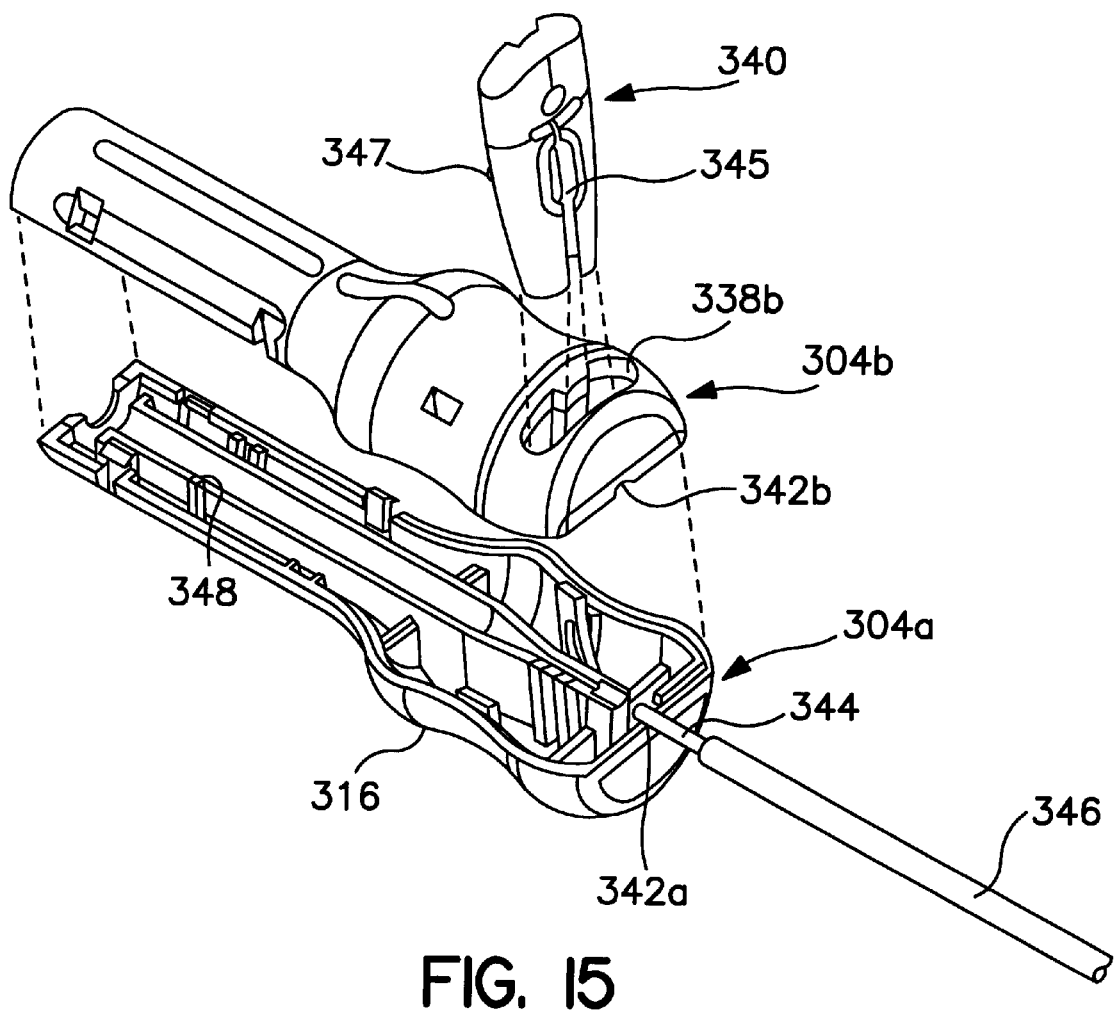
FIG. 15 is a perspective diagram of first and second halves of the attachment of the embodiment of FIG. 14, and further includes the pushbutton clevis.

FIG. 15 is a perspective diagram of first and second halves 304a and 304b, respectively, of the attachment of the embodiment of FIG. 14, and further includes pushbutton 340. Pushbutton 340 is adapted to slidably engage within recess 338b of attachment half 304b, and to further engage in recess 338a (not shown in this view) of attachment half 304a when the attachment halves are coupled together as shown by the dashed lines of FIG. 15. The pushbutton is prevented from falling out of recesses 338b by a locking pin 347 shown protruding perpendicularly from a proximal face of the pushbutton. When inserted within the recess, the pushbutton generally resides in either a first loose position, or a second locked position.

Each of the attachment halves further includes a cut-away area 342a and 342b on the distal face of cylindrical knob 316 of attachment halves 304a and 304b, respectively. This cutaway area accommodates the positioning of a lead connector pin 344 of an implantable lead 346. When the pushbutton is in the loose position, the connector pin 344 of lead 346 may be easily inserted into this cutaway area. Once the lead connector is so positioned, the pushbutton may be snapped into the locked position such that pushbutton 340 traps connector pin 344 within one end of aperture 345. This fixes the implantable lead 346 in a rigid position with respect to the attachment. Rotation of the cylindrical knob 316 will now rotate the entire lead body, allowing for easy fixation of a helical screw that may be carried at the distal end of the lead body within adjacent tissue. This pushbutton mechanism is further discussed below.

FIG. 15 further shows the coupling mechanism 348 that is provided to couple to notches 336 included within pin 334. In one embodiment, this coupling mechanism is a protrusion 348 that may be included on one or both of the attachment halves 304*a* and 304*b*. This protrusion is adapted to fit within any of notches 336 to allow the attachment to be selectably positioned at regular intervals along pin 334.

Modifications to the embodiments discussed above are permissible within the scope of the invention, and the possibility of such modification should be understood in conjunction with the claims that follow.

What is claimed is:

1. A stylet for guiding leads and catheters, comprising:
   a deflectable outer member;
   a braided structure located adjacent to at least a distal portion of the outer member to provide added torsional strength to the at least distal portion of the outer member, wherein the distal portion of the outer member is formed of a first material having superelastic properties, and wherein the outer member further includes a proximal portion located adjacent to the distal portion and formed of a second material that is different from the first material.

2. The stylet of claim 1, and further comprising a pull-wire located within the outer member to facilitate deflection of the distal portion of the outer member.

3. The stylet of claim 1, wherein the first material is a nickel titanium alloy.

4. The stylet of claim 1, wherein the second material has a greater torsional strength than the first material.

5. The stylet of claim 1, wherein the braided structure includes a metal braid.

6. The stylet of claim 5, wherein the metal braid is formed of a metal ribbon wire.

7. The stylet of claim 6, wherein the metal ribbon wire is stainless steel.

8. The stylet of claim 6, wherein the metal braid is reinforced with a polyimide.

9. The stylet of claim 6, wherein the metal braid has a pick count between 100 and 160 picks per inch.

10. The stylet of claim 1, wherein the diameter of the stylet is no greater than 0.025 inches.

11. The stylet of claim 1, wherein the braided structure is located adjacent to the entire length of the outer member.

12. The stylet of claim 1, wherein the outer member is formed of stainless steel.

13. The stylet of claim 2, wherein the distal portion of the outer member includes at least one aperture to provide a preferred deflection direction.

14. The stylet of claim 13, wherein the at least one aperture is an elongated slot substantially parallel to the axis of the outer member.

15. The stylet of claim 1, and further comprising a handle located at the proximal end of the outer member.

16. The stylet of claim 15, wherein the handle includes a rotatable member to deflect the distal portion of the outer member.

17. The stylet of claim 15, wherein the handle includes a member that is slidable longitudinally to deflect the distal portion of the outer member.

18. The stylet of claim 15, wherein the handle is adapted to be coupled to a lead into which the outer member has been inserted.

19. The stylet of claim 15, and further including a lead extension tool slidably coupled to the handle, the lead extension tool to further couple to a lead into which the outer member has been inserted to adapt the lead length to the length of the outer member.

20. The stylet of claim 5, wherein the metal ribbon wire is a precipitation-hardening stainless steel.

21. The stylet of claim 5, wherein the metal ribbon wire is primarily molybdenum.

22. The stylet of claim 12, wherein the outer member is formed of a precipitation-hardening stainless steel.

23. A stylet for guiding leads and catheters, comprising:
    a deflectable outer member;
    a braided structure located adjacent to at least a distal portion of the outer member to provide added torsional strength to the at least distal portion of the outer member; and
    a pull-wire located within the outer member to facilitate deflection of the distal portion of the outer member, wherein the distal portion of the outer member includes at least one aperture to provide a preferred deflection direction.

* * * * *